United States Patent [19]
Ariga et al.

[11] Patent Number: 5,814,494
[45] Date of Patent: Sep. 29, 1998

[54] PROCESS FOR IMPROVING THE PROPERTY OF PROANTHOCYANIDINS AND FOR PREPARING AN IMPROVED PROANTHOCYANIDIN PRODUCT

[75] Inventors: Toshiaki Ariga, Noda; Hiroshi Hosoyama, Tokyo; Katsumi Yuasa, Funabashi, all of Japan

[73] Assignee: Kikkoman Corporation, Noda, Japan

[21] Appl. No.: 601,456

[22] Filed: Feb. 14, 1996

[30] Foreign Application Priority Data

Feb. 15, 1995 [JP] Japan .................................. 7-049333

[51] Int. Cl.$^6$ ...................... A23L 3/3544; C07D 311/62; C09K 15/08; C12P 17/06
[52] U.S. Cl. .......................... 435/118; 435/125; 435/158; 435/197; 435/918; 426/545
[58] Field of Search .................... 435/158, 118, 435/125, 197, 918; 426/545

[56] References Cited

U.S. PATENT DOCUMENTS

| | | | |
|---|---|---|---|
| 3,812,266 | 5/1974 | Sanderson et al. | 426/52 |
| 5,159,069 | 10/1992 | Hirayama et al. | 536/118 |

FOREIGN PATENT DOCUMENTS

| | | |
|---|---|---|
| 0 307 071 A2 | 3/1989 | European Pat. Off. . |
| Kokoku No. 3-7232 | 7/1984 | Japan . |

OTHER PUBLICATIONS

S.M. Lunte, et al., "Detection and Identification of Procyanidins and Flavonols in Wine by Dual–Electrode Liquid Chromatography–Electrochemistry", Analyst 1988, vol. 13, No.1. pp. 99–102.

G. Nonaka, et al., "Tannins and Related Compounds", Chem. Pharm. Bull. 1983, vol. 31, No. 11, pp. 3906–3914.

F. Hashimoto, et al., "Tannins and Related Compounds", Chem. Pharm. Bull. 1989, vol. 37, No. 12,, pp. 3255–3263.

G. Giovanelli, "Enzymic Treatment of Malt Polyphenols for Beer Stabilization", Chemical Abstracts 1990, vol. 112, No. 17, pp. 578, col. 2.

G. Meirelles, et al., "Estimation of Galloylated Procyanidins in Red Wines Produced by Different Methods of Vinification", Chemical Abstracts 1992, vol. 123, No. 13, pp. 915, col. 2.

ABS Derwent Japio 86–016982/AN Ariga et al (J61016982) Jan. 24, 1986.

ABS Derwent WPIL 91–300280/41/AN Kikkoman Corp (J03200781) Sep. 2, 1991.

ABS Derwent WPIL 94–347352/43/AN Nikken Food KK (JP06271850) Sep. 27, 1994.

Derwent ABS WPIL 95–036448/05/AN Bignon et al. (WO9429401) Dec. 22, 1994.

Derwent ABS WPIL 86–065473/10/AN Kikkoman Corp. (J61016982) Jan. 10, 1989.

Derwent ABS WPIL 88–230489/33/AN Kikkoman Corp (J63162685) Jul. 6, 1988.

Derwent ABS WPIL 76–06271X/04/AN Kikkoman Corp(J50101581) Aug. 17, 1976.

*Primary Examiner*—Herbert J. Lilling
*Attorney, Agent, or Firm*—Banner & Witcoff, Ltd.

[57] ABSTRACT

The present invention is directed to a process for improving the property of proanthocyanidins comprising contacting the proanthocyanidin containing solution with tannase and a process for increasing the yield of proanthocyanidins comprising contacting the proanthocyanidin containing solution with tannase in the extraction of the proanthocyanidins.

2 Claims, No Drawings

PROCESS FOR IMPROVING THE PROPERTY OF PROANTHOCYANIDINS AND FOR PREPARING AN IMPROVED PROANTHOCYANIDIN PRODUCT

BACKGROUND OF THE INVENTION

1. Field of the Invention

The present invention relates to a process for improving the property of proanthocyanidins using a tannase and a process for preparing an improved proanthocianidin product.

2. Description of the Related Art

The proanthocyanidins are a group of compounds bonded by condensation or polymerization of condensed type tannin, that is, flavan-3-ols or flavan-3,4-diols which are present in various plants, as constitutional units. Those compounds may be treated with an acid to form anthocyanidins such as cyanidin, delphinidin and pelargonidin. From such a fact, the compounds are given by this name. The compounds include proanthocyanidins such as higher molecular procyanidin, prodelphinidin and propelargonidin, and their stereoisomers or the like which are dimers, trimers, tetramers or decamers.

The present inventors have discovered that the proanthocyanidins have a strong antioxidative action and filed a patent application (Patent Kokoku No. 3-7232).

However, the proanthocyanidins have rather astringent taste and when the compounds are used as an anti-oxidant for foodstuff, the resulting food product becomes astringent. Thus, there is an inconvenience that its application is restricted owing to the type of food products.

The present inventors have studied for the purpose of reducing the astringency in proanthocyanidins and found that the preferred effects may be obtained by subject a proanthocyanidin containing solution to action of tannase. Additionally, the present invention provides also a process for preparing a high quality proanthocyanidin product in a high yield.

SUMMARY OF THE INVENTION

The proanthocyanidin containing solution to which the present invention intends includes an aqueous solution, aqueous alcoholic solution or the like obtained by extracting various plants such as grape seeds, cranberries, apples, adzuki beans, and the barks of Japanese ceder and Japanese cypress, for example, extracts before or after filtration in water-extraction step or an aqueous solution obtained by dissolving proanthocyanidins which have been concentrated, separated and purified after extraction in water.

Tannase used in the present invention may be known one, for example, tannase obtained by incubating a microorganism belonging to *Aspergillus oryzae* (see Patent Kokoku No. 56-8584).

The conditions for acting tannase may be varied by the temperature and pH, for example, the temperature and pH of the proanthocyanidin containing solution are adjusted to 20° to 60° C. and pH 2 to 7, respectively and the tannase may be added to the solution. The time for acting the enzyme is 5 minutes or more, preferably 30 minutes or more. The amount of tannase added is one unit, preferably 5 units or more per gram of proanthocyanidins. The concentration of proanthocyanidins in the proanthocyanidin containing solution is 0.01 to 20% by weight.

The astringency in proanthocianidins may be largely reduced by doing said process and it may be used for any food materials without hindrance.

The present invention is explained with reference to Examples. The quantitative determination of proanthocyanidins was carried out using R. Jambunathan et. al.'s method (J. Agric. Food Chem., 34, 425–429, 1986), wherein a sample containing proanthocyanidin is heated in the presence of dilute HCl to redden the proanthocyanidins, and proanthocyanidins are quantitatively determined from the measurements of absorbence at 550 nm and calibration curve made from a procyanidin tetramer as a standard sample which was separated and purified from a cider according to A.G.H. Lea's method.

DESCRIPTION OF THE PREFERRED EMBODIMENTS

EXAMPLE 1

Grape seeds (species: Liesling) were extracted with hot water to obtain an extract followed by dehydration. 100 g of the resulting dehydrated extract (proanthocyanidin content: 40%) were dissolved in 20 liters of water, adjusted to pH 5.5 with sodium hydrogen carbonate and 0.08 g (about 10 units/g of proanthocyanidins) of tannase (5000 units/g, a product of Kikkoman Corp.) was added therein to act at 30° C. for 2 hours while stirring. The mixture was treated at 60° C. for 20 minutes to inactivate the enzyme. The treated solution of proanthocyanidins was organoleptically tested according to the following procedures.

Said treated solution was adjusted to 0.02% of the proanthocyanidin concentration and the astringency was assessed by 20 panels in comparison with no tannase treatment as a control.

The assessment was carried out using 7 scores of −3, −2, −1, 0, +1, +2, +3, wherein 0 is the same order as the control, −3 is the strongest astringency, and +3 is highly weak astringency. The average score of the panels was +0.810, standard deviation was 0.744 and level of significance was less than 5%. Accordingly, it was confirmed that the treated solution was assessed to be significantly weak in astringency and the treatment with tannase was useful for reducing astringency in proanthocyanidins.

EXAMPLE 2

Grape seeds (species: Liesling) were washed with water of 4 times at a temperature of 60° C. for 2 hours and extracted with water of 4 times at 80° C. for 2 hours. The resulting extract was cooled to 45° C. The pH of the extract is 4.7, the concentration of proanthocyanidins in the solution and the solid concentration were 0.63% and 0.69%, respectively.

The same tannase as one used in Example 1 was added to said extract, so that the unit of tannase may reach 10 units/g of proanthocyanidins and the mixture was reacted at 45° C. for 1 hour while stirring.

The mixture was treated at 60° C. for 20 minutes to inactivate the enzyme and cooled to 25° C. The product was organoleptically tested similarly to Example 1. The average score of 20 panels was +0.690, a standard deviation was 0.554, a level of significance was less than 5%. Accordingly, it was confirmed that the treated solution was assessed to be significantly weak in astringency and the treatment with tannase was useful for reducing astringency in proanthocyanidins.

Even when the time of treatment with the enzyme was 30 minutes, similar results were obtained.

When tannase is reacted with the proanthocyanidin containing solution, the astringency may be reduced by using an extract in which the concentration of solid in the extract has been concentrated to 5 to 20% and the yield of the proanthocyanidins may be increased.

EXAMPLE 3

Grape seeds (species: Liesling) were extracted with 50% ethanol of 5 times at a temperature of 50° C. for one week, the extract was concentrated to the solid concentration of 10% to remove the alcohol therefrom. To 1 liter of the concentrated solution was added tannase of about 10 units/g of proanthocyanidins, the mixture was reacted for 2 hours while stirring followed by centrifugal separation to remove precipitates. The resulting supernatant liquid was conventionally concentrated and freeze-dried to obtain the powdered product of the proanthocyanidins.

For the control purpose, a powdered product of proanthocyanidins was obtained using the same procedure as that as mentioned above, except that tannase was not added. The results are shown below.

|  | Tannase Treatment (present Invention) | No Tannase (Control) | Treatment Present Invention/ Control (%) |
|---|---|---|---|
| Yield of Product (g) | 96.1 | 84.5 | 114 |
| Amount of proanthocyanidin in the Product (g) | 42.9 | 32.4 | 132 |
| Astringency (*) | Average Score Standard deviation | | +0.752 0.562 |

*: The assessment of the astringency was carried out according to the same method as that of example 1, namely 7 scores method.

As is clear from the results in Example 3, the proanthocyanidins obtained by the present invention have reduced astringencies and the yield was largely increased (+32%) as compared with a control.

In view of said facts, it is considered that an ester bonding of a dimer procyanidin B-1 gallic acid ester or a dimer prodelphinidin B-2 gallic acid ester is cleaved by tannase to form a procyanidin B-1 or prodelphinidin B-2 and gallic acid, thereby insolublized proanthocyanidins are reduced because the water solubility and affinity with other components have been changed and a larger amount of proanthocyanidins could be recovered in the supernatant liquid.

EXAMPLE 4

Grape seeds (species: Chardonnay) were extracted in water of 5 times at a temperature of 90° C. for 2 hours and the extract was cooled to 40° C. The pH of this extract was 4.7 and the concentrations of proanthocyanidins and of solid content in the solution were 0.70% and 2.20%, respectively. The same tannase as one in Example 1 was added to the extract, so that the unit of tannase may reach 15 units/g of proanthocyanidins and the mixture was reacted at 40° C. for 1 hour while stirring. The mixture was pasteurized at 85° C. for 30 minutes to inactivate the enzyme, and concentrated at 40° C. or less under reduced pressure and freeze-dried to obtain a dry powder containing proanthocyanidins. The resulting product was very weak in astringency, as compared with one of no tannase treatment.

EXAMPLE 5

White grape (species: Chardonnay) was compressed to 25% of yield to obtain a compressed refuse. To 1000 g of the refuse (calculated as anhydride) was added 10 liters of water at 40° C. followed by stirring and filtering to remove water-soluble substances. Ten liters of water at 40° C. were added to the residues and extracted at the same temperature for 3 hours while stirring followed by filtering to obtain an extract. The concentrations of proanthocyanidins and solids in this extract at 90° C. were 0.18% and 0.60%, respectively. The extract was concentrated at 40° C. or less under reduced pressure followed by freeze-drying to obtain a powdered product of proanthocyanidins.

The product 100 g was dissolved in water to 500 ml and 0.06 g (about 10 units/g of proanthocyanidins) of tannase (5000 units/g, a product of Kikkoman Corp.) was added thereto. The resulting mixture was reacted at 35° C. for 4 hours while stirring and the enzyme was inactivated at 85° C. for 30 minutes. The aqueous proanthocyanidin solution thus obtained had a reduced astringency. Additionally, the powder of proanthocyanidins obtained by concentrating and freeze-drying the solution was also not astringent.

EXAMPLE 6

White grape seeds (species: Chardonnay) was extracted with 20% ethanol solution of 3 times for 2 hours followed by filtering. The resulting extract was concentrated to 5% of solid concentration to remove ethanol. To 1 liter of the concentrated solution (pH 4.6) was added 0.05 g (about 10 units/g of proanthocyanidins) of tannase (5000 units/g, a product of Kikkoman Corp.). The mixture was reacted at 30° C. for 6 hours followed by centrifugal separation to remove a precipitate and the supernatant liquid having 2.37% of proanthocyanidin concentration and 4.74% of solid concentration was obtained. The supernatant liquid was concentrated at 40° C. or less under reduced pressure followed by freeze-drying to obtain a powdered proanthocyanidin product.

The powder of proanthocyanidins obtained by concentrating and freeze-drying the solution was not astringent.

We claim:

1. A process for preparing proanthocyanidins having a reduced astringency which comprises extracting grape seeds with water or an organic solvent to obtain a proanthocyanidin-containing solution; adding tannase to the resulting proanthocyanidin-containing solution or to a concentrated solution thereof for reaction therewith; and after reaction with tannase, separating the solution into a solid and a liquid phase, concentrating the liquid phase, heat-pasteurizing the liquid phase and, drying and optionally powdering the liquid phase.

2. A process for preparing proanthocyanidins having a reduced astringency which comprises extracting grape seeds with water or an organic solvent to obtain a proanthocyanidin-containing solution; concentrating the proanthocyanidin-containing solution to a solids concentration of 5–20%; adding tannase to the concentrated solution for reaction therewith; after reaction with tannase, separating the tannase reacted solution into a solid and a liquid phase; and then concentrating, heat-pasteurizing and drying the resulting liquid phase to give a powdered product.

* * * * *